US006235265B1

(12) United States Patent
Logsdon

(10) Patent No.: US 6,235,265 B1
(45) Date of Patent: May 22, 2001

(54) EVAPORATIVE COOLANT FOR TOPICAL ANESTHESIA COMPRISING HYDROFLUOROCARBONS AND/OR HYDROCHLOROFLUOROCARBONS

(75) Inventor: Peter B. Logsdon, Orchard Park, NY (US)

(73) Assignee: AlliedSignal Inc., Morristown, NJ (US)

( * ) Notice: Subject to any disclaimer, the term of this patent is extended or adjusted under 35 U.S.C. 154(b) by 0 days.

(21) Appl. No.: 09/181,174

(22) Filed: Oct. 28, 1998

(51) Int. Cl.$^7$ .................................................. A61K 9/12
(52) U.S. Cl. ............................ 424/45; 424/47; 514/817
(58) Field of Search ....................... 424/45, 47; 514/817

(56) References Cited

U.S. PATENT DOCUMENTS

| | | |
|---|---|---|
| 4,174,295 * | 11/1979 | Bargigia et al. . |
| 4,865,028 | 9/1989 | Swart . |
| 5,225,183 | 7/1993 | Purewal et al. . |
| 5,397,564 * | 3/1995 | Seki et al. . |
| 5,496,866 | 3/1996 | Sommerfield et al. . |
| 5,574,192 | 11/1996 | VanDerPuy et al. . |
| 5,589,156 | 12/1996 | Henry . |
| 5,593,566 | 1/1997 | Henry . |
| 5,679,325 | 10/1997 | Henry . |
| 5,710,352 | 1/1998 | Tung . |
| 5,800,729 | 9/1998 | Singh et al. . |
| 5,925,612 * | 7/1999 | Lund et al. . |

FOREIGN PATENT DOCUMENTS

| | | |
|---|---|---|
| 2075060 * | 1/1991 | (CA) . |
| 2782639 | 3/2000 | (FR) . |
| 1212942 | 11/1970 | (GB) . |
| WO95/04022 | 2/1995 | (WO) . |
| 95/08603 | 3/1995 | (WO) . |
| 96/12442 | 5/1996 | (WO) . |
| 96/18384 | 6/1996 | (WO) . |

OTHER PUBLICATIONS

"The Myofascial Genesis of Pain"; from *Postgraduate Medicine*, vol. 11, No. 5, May 1952; Janet Travell and Seymour H. Rinzler; Cornell University Medical College and Beth Israel Hospital, New York.

"Ethyl Chloride Spray for Painful Muscle Spasm"; from *Physical Medicine*, May 1952; Janet Travell, M.D.; New York, New York.

"Factors Affecting Pain of Injection"; from *Journal of the American Medical Association*, vol. 158, pp. 368–371, Jun. 4, 1955; Janet Travell, M.D.; New York, New York.

"How to Give Painless Injections"; from a Scientific Exhibit, Section on Pediatrics, American Medical Association, Jun. 3–7, 1957; New York, New York; given by Virginia D. Weeks, M.D. and Janet Travell, M.D., Departments of Pediatrics and of Pharmacology, The New York Hospital, Cornell Medical Center, New York.

"Evaluation and Treatment of Muscle Function in Athletic Injury"; from *American Journal of Surgery*, vol. 98, No. 3, pp. 353–362, Sep. 1959; Hans Kraus, M.D.; New York, New York.

"'Spray–and–Stretch' Treatment for Myofascial Pain"; from *Hospital Physician*, Dec. 1973; John McM. Mennell, M.D.; Medical Economics Company, Oradell, New Jersey.

"Cryotherapy in Sports Medicine"; from *Scandinavian Journal of Medicine and Science in Sports*; vol. 6, pp. 193–200, Apr. 18, 1996; C Swanson, L. Swärd and J. Karlsson; Department of Orthopaedics, Ostra University Hospital, Goteborg, Sweden.

* cited by examiner

*Primary Examiner*—Raj Bawa
(74) *Attorney, Agent, or Firm*—Colleen D. Szuch; Marie Collazo

(57) ABSTRACT

Evaporative coolants suitable for use as cold spray topical anesthetics containing hydrofluorocarbons and/or hydrochlorofluorocarbons, preferably 1,1,1,3,3-pentafluoropropane, either alone or in combination with other hydrofluorocarbon and/or hydrochlorofluorocarbon components. The invention includes a system for cooling skin using the coolant and a device for spraying the coolant, as well as a method of cooling or topically anesthetizing the skin comprising spraying such evaporative coolants thereon.

6 Claims, 4 Drawing Sheets

EVAPORATIVE COOLANT FOR TOPICAL ANESTHESIA COMPRISING HYDROFLUOROCARBONS AND/OR HYDROCHLOROFLUOROCARBONS

FIELD OF THE INVENTION

The invention relates to evaporative coolants, and more particularly to evaporative coolants suitable for use as cold spray topical anesthetics comprising hydrofluorocarbons and/or hydrochlorofluorocarbons, preferably 1,1,1,3,3-pentafluoropropane, either alone or in combination with other components, and to a method of cooling or topically anesthetizing the skin comprising spraying such coolants thereon.

BACKGROUND OF THE INVENTION

Topical anesthetics are products which are applied to skin or mucous tissue of warm-blooded animals to cause temporary numbness at the site of application. One type of topical anesthetic is a liquid evaporative coolant or cold spray which relies on the cooling effect of evaporation to anesthetize nerves. This type of product is used for minor surgical procedures, such as lancing boils or drainage of small abscesses. The application of cold, referred to as cryotherapy, is also used in the treatment of injury or disease, and is particularly widespread in sports medicine.

Ethyl chloride in a spray bottle reportedly has been marketed as a cold spray topical anesthetic since early in the twentieth century, and this product has remained essentially unchanged. When liquid ethyl chloride is sprayed on skin, the ethyl chloride rapidly evaporates and chills the skin to anesthetize the nerves. The cooling effect is due to the heat of vaporization of the boiling liquid. One reason that ethyl chloride is suitable for this purpose is its boiling point of 12.3° C. This boiling point is low enough to cause rapid vaporization on contact with body temperature skin. Yet, the boiling point is high enough to allow the liquid to be kept in a simple sealed container at room temperature, and to allow the anesthetic to be used without damaging the skin.

Currently marketed cold spray anesthetics include pure ethyl chloride spray, as well as blends of ethyl chloride with CFC-114 (dichlorotetrafluoroethane), CFC-114 by itself, and a CFC-11 (trichlorofluoromethane)/CFC-12 (dichlorodifluoromethane) blend. However, there are problems in the use of all of these materials. Because of environmental considerations, chlorofluorocarbons (CFCs) such as CFC-114, CFC-11 and CFC-12 are all being phased out. This leaves only the ethyl chloride coolant spray. However, ethyl chloride is a highly flammable liquid which volatizes at room temperature to form an explosive gas. Upon combustion, ethyl chloride can form hydrogen chloride or even highly toxic phosgene ($CCl_2O$). Furthermore, ethyl chloride can react with hot water or steam to form hydrogen chloride or hydrochloric acid. For these reasons, extreme caution must be used when handling and using ethyl chloride.

Thus, there is a need for other materials which can be used as evaporative coolant sprays in place of ethyl chloride, and which are free of the environmentally unacceptable chlorofluorocarbons used in existing products.

DESCRIPTION OF THE INVENTION

The present invention provides a liquid evaporative coolant comprising at least one hydrofluorocarbon (HFC) or hydrochlorofluorocarbon (HCFC), either alone or in combination with other environmentally acceptable components. Such liquid evaporative coolants are suitable for use as cold spray topical anesthetics. For effectiveness and safety as a cold spray for skin, the coolant should have a boiling point in the range of about −10° C. to about 25° C., preferably from about 0° C. to 20° C. It is believed that a coolant with a boiling point below about −10° C. may cause localized freezing of the skin or even frostbite. Even coolants with higher boiling points, such as ethyl chloride, can cause such freezing if not used properly. The coolant of the present invention preferably comprises at least about 50 weight percent of such HFC and/or HCFC components, more preferably at least about 90 weight percent, and most preferably consists essentially of such components. Throughout this application, all percentages shall be by weight unless stated otherwise.

The present invention includes a system for cooling skin, the system comprising the evaporative coolant and a device for dispensing a liquid spray of the coolant. To be effective as a cold spray, the coolant must be sprayed in liquid form onto the skin, where it vaporizes by drawing heat from the surface of the skin being cooled. Preferably, the spray device disperses a fine, controlled spray of the coolant to allow rapid evaporation and cooling on the selected portion of skin.

Figure 1:
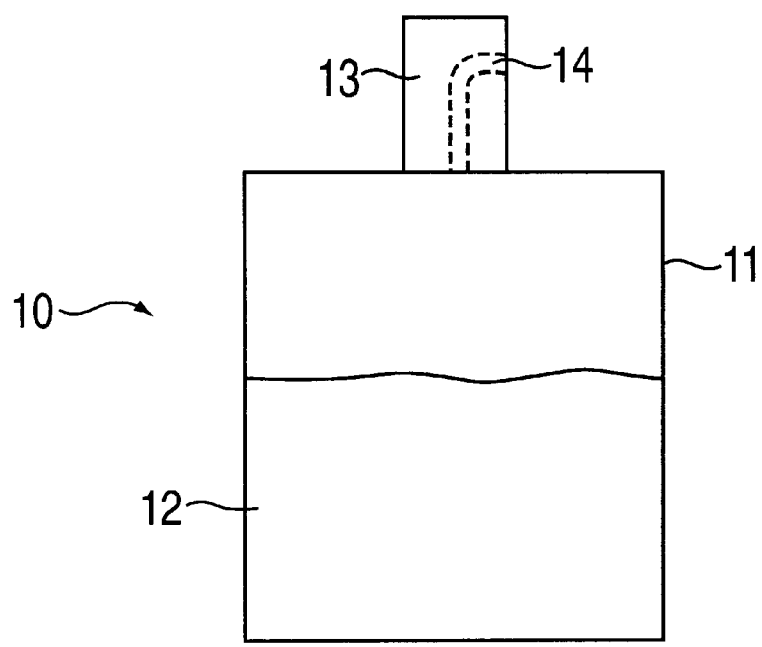
FIG. 1 is a schematic representation of a device for dispensing a liquid spray while in the inverted position.

Spray bottles and other containers suitable for such purposes are well known in the art. FIG. 1 is a schematic representation of a device 10 for dispensing a liquid 12 from a container 11, while the container is in an inverted position. To apply the spray from such a device, the container is first inverted, so that the liquid is in contact with one end of a lumen 14 which passes through a spray valve 13. The valve is then actuated to spray the liquid through lumen 14.

Figure 2:
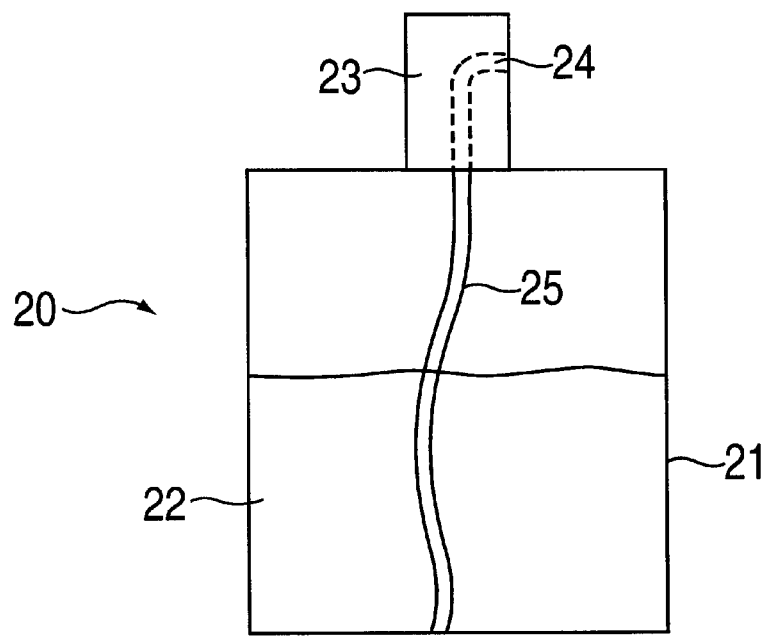
FIG. 2 is a schematic representation a device for dispensing a liquid spray while in the upright position.

FIG. 2 is a schematic representation of an alternative spray device 20 which is intended to be used in the upright position. Container 21 contains liquid 22, and is fitted with a spray valve 23, which includes a lumen 24 passing there-through. A tube 25 extends from one end of lumen 24 to the bottom of the container. The valve is actuated while the container is in an upright position, and the fluid is drawn through tube 25 and dispersed through lumen 24.

In other embodiments of the devices of either FIGS. 1 or 2, the container can be made of a flexible material, and squeezed to propel the liquid through the lumen. Alternatively, the spray can be propelled by the use of a separate squeeze bulb, as of the type commonly used on perfume bottles. Other variations of such spray devices will be apparent to those skilled in the art.

For purposes of this application, the following definitions will be used for carbon-based compounds. Hydrocarbons are organic compounds consisting exclusively of the elements carbon and hydrogen. Hydrofluorocarbons are compounds which consist exclusively of carbon, hydrogen and fluorine, and must contain at least one fluorine atom. Perfluorocarbons (PFCs) are compounds which consist of only carbon and fluorine. Hydrochlorofluorocarbons are compounds which consist exclusively of carbon, hydrogen, chlorine and fluorine, and must include at least one of each atom. Chlorofluorocarbons (CFCs) consist exclusively of carbon, chlorine and fluorine and do not have any hydrogen atoms.

Under present standards HFCs and HCFCs are considered environmentally acceptable. However, the use of HCFCs may be phased out in the coming years, depending on their chlorine content and perceived effects on atmospheric ozone. The acceptability of perfluorocarbons (PFCs) varies with the specific PFC and the application for which it is to be used. PFCs may be used in the compositions of the present invention, if they are considered environmentally acceptable. On the other hand, CFCs are considered environmentally unacceptable, and their various uses have been banned or are being phased out. For these reasons, the compositions of the present invention are preferably free of all CFC compounds. More preferably, the compositions are also free of HCFC compounds, particularly those which are considered to be environmentally unacceptable. Therefore, in a preferred embodiment, the composition of the present invention consists essentially only of HFC compounds. As discussed above, preferably the composition also is free of ethyl chloride, or any other flammable or environmentally unacceptable compounds. For purposes of this application, a composition shall be considered substantially free of a component when it contains less than about 0.5 weight percent of that component.

A preferred hydrofluorocarbon for use in the present invention is 1,1,1,3,3-pentafluoropropane (HFC-245fa). HFC-245fa is a well-known, environmentally acceptable hydrofluorocarbon which has been identified as a foam blowing agent, an aerosol propellant, a heat transfer agent, and a possible replacement for CFC-11 in refrigeration systems. It has a boiling point of about 15.3° C. and a relatively high heat of vaporization. As a result, it acts as an evaporative coolant in much the same way as ethyl chloride, which has a boiling point of 12.3° C. Yet, HFC-245fa is non-flammable and non-reactive with water. It can therefore be used without the safety concerns associated with ethyl chloride.

HFC-245fa may be manufactured by various processes, such as those set forth in VanDerPuy et al., U.S. Pat. No. 5,574,192, Tung, U.S. Pat. No. 5,710,352, and VanDerPuy et al., PCT Publication WO95/04022, all of which are incorporated herein by reference.

As previously mentioned, HFC-245fa boils at 15.3° C., which makes it suitable for use as an evaporative coolant by itself. However, the boiling point can be raised or lowered by the addition of one or more other components with higher or lower boiling points. Decreasing the boiling point of the composition will increase the vapor pressure, and increasing the boiling point will decrease the vapor pressure.

The boiling point of the evaporative coolant should be in the range of about −10° C. to about 25° C. Preferably, the boiling point is at least about 0° C. and less than about 20° C. A mixture with too low a boiling point may cause localized skin freezing or frostbite, while a mixture with too high a boiling point would not be effective enough for skin cooling. By selectively adding components with lower boiling points, the boiling point of the composition may be adjusted as desired. For instance, the boiling point of a composition comprising HFC-245fa, which boils at 15.3° C., can be lowered to match closely with the 12.3° C. boiling point of ethyl chloride.

When different hydrofluorocarbons and hydrochlorofluorocarbons are combined, they should be compounds which are fully miscible with each other. Preferably, the coolant comprises at least about 50 weight percent hydrofluorocarbons, more preferably at least about 90 weight percent, and even more preferably consists essentially of hydrofluorocarbons. When hydrochlorofluorocarbons are included in the coolant, preferably they are ones which are considered environmentally acceptable. Because of the continual re-evaluation of what is considered environmentally acceptable, the selection of such compounds for inclusion in the coolant should be made in view of then current regulations or scientific findings.

Table I lists HFC and HCFC compounds with lower boiling points than HFC-245fa which are considered particularly suitable for forming reduced boiling point mixtures with HFC-245fa, which is also listed. Preferably, such mixtures contain at least about 50 weight percent HFC-245fa. The formula is given for each compound, and they are listed in order of boiling point (B.P.):

TABLE I

| Compound | Formula | B.P. (° C.) |
| --- | --- | --- |
| HFC-134a | $CF_3CH_2F$ | −26.1 |
| HFC-134 | $CF_2HCF_2H$ | −19.6 |
| HFC-227ea | $CF_3CFHCF_3$ | −16.5 |
| HFC-227ca | $CF_2HCF_2CF_3$ | −15.5 |
| HCFC-124 | $CF_3CHFCl$ | −12.1 |
| HCFC-142b | $CF_2ClCH_3$ | −9.8 |
| HFC-236fa | $CF_3CH_2CF_3$ | −1.4 |
| HFC-254cb | $CH_3CF_2CF_2H$ | −1.0 |
| HFC-236cb | $CFH_2CF_2CF_3$ | −0.8 |
| HFC-236ea | $CF_3HCFHCF_3$ | 6.1 |
| HFC-236ca | $CF_2HCF_2CF_2H$ | 13.3 |
| HFC-245fa | $CF_3CH_2CF_2H$ | 15.3 |

Based on their boiling points, HFC-236ea (1,1,2,3,3,3-hexafluoropropane) and HFC-236ca (1,1,2,2,3,3-hexafluoropropane) are also preferred compounds for use as cooling spray anesthetics, either alone or in combination with other environmentally acceptable components.

EXAMPLE 1

Figure 3:
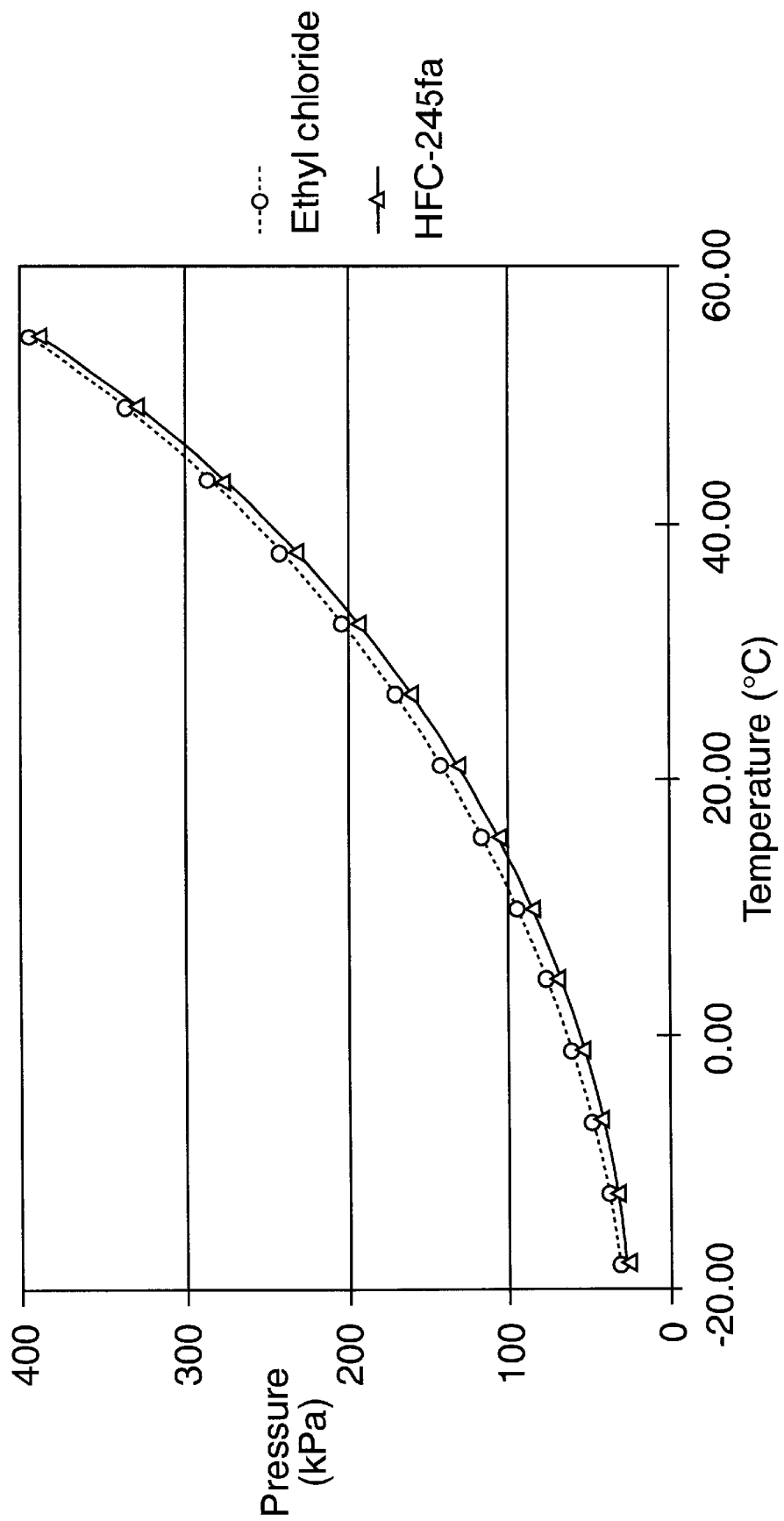
FIG. 3 is a graph comparing the vapor pressures of ethyl chloride and 1,1,1,3,3-pentafluoropropane.

Tests were conducted to compare the vapor pressure of HFC-245fa to the reported vapor pressure data for ethyl chloride (see *The Properties of Gases and Liquids*, 4th Edition, R. C. Reid, J. M. Prausnitz and B. E. Poling, McGraw-Hill, Inc. 1987, p. 677. The results presented in FIG. 3 show that the vapor pressure of HFC-245fa is slightly lower than that of ethyl chloride.

EXAMPLE 2

An experiment was conducted to compare the cooling effect of HFC-245fa to ethyl chloride. An Omega type T thermocouple for measuring temperature was taped to a small sheet of plastic. The thermocouple was connected to a Fisher Scientific chart recorder that measured the change in temperature versus time. Approximately two grams of ethyl chloride was sprayed onto the tip of the thermocouple over 45 seconds. The resulting change in temperature was measured over 30 minutes. Once the thermocouple equilibrated to room temperature, this experiment was repeated for HFC-245fa. The results are presented in FIG. 4.

EXAMPLE 3

Another experiment was conducted in the same manner as Example 2, except the amount sprayed on the thermocouple was increased to four grams, both for the ethyl chloride and the HFC-245fa. These results are presented in FIG. 5.

Figure 4:
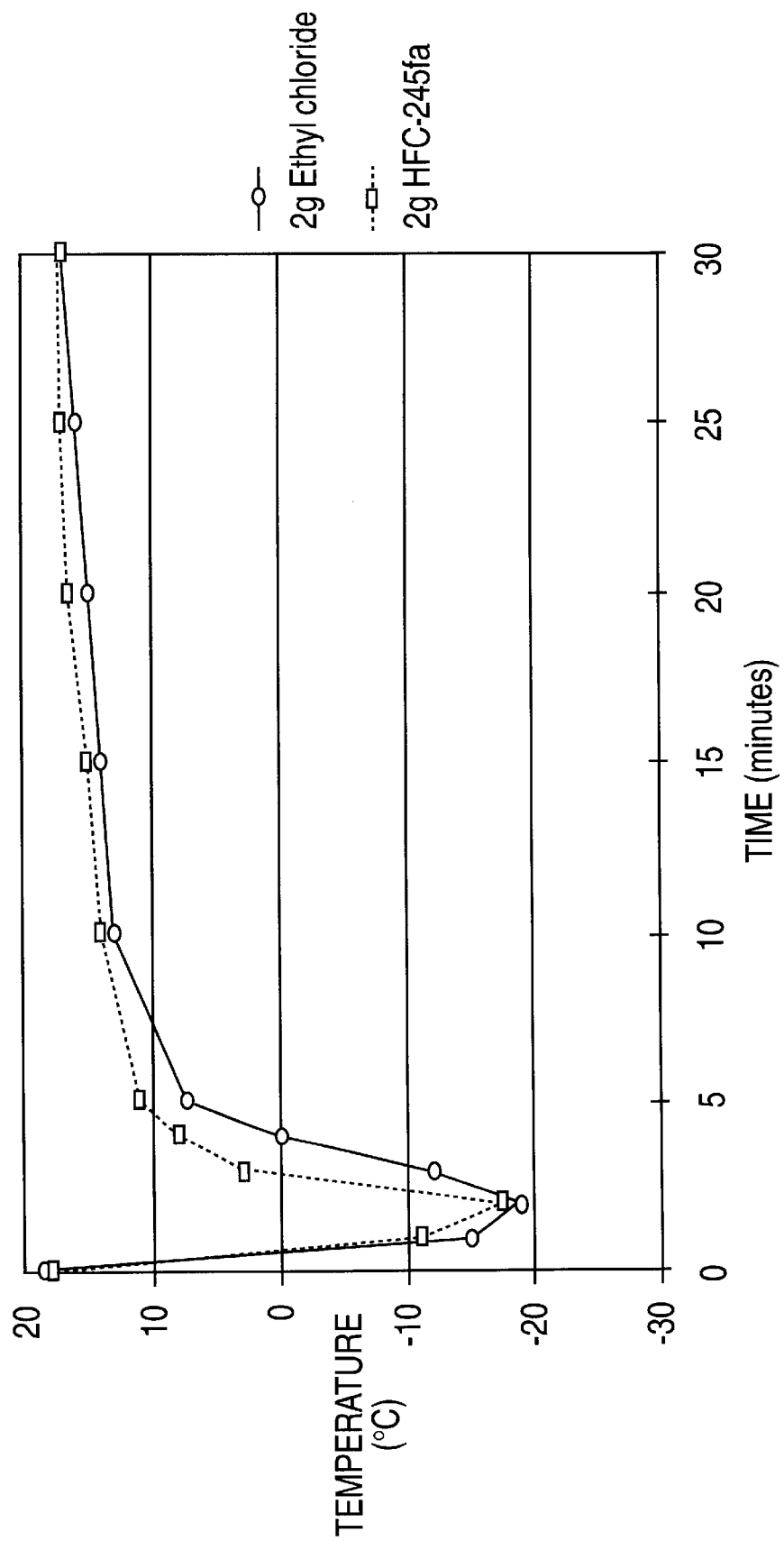
FIG. 4 is a graph comparing the cooling effects of ethyl chloride and 1,1,1,3,3-pentafluoropropane at two grams loading.
Figure 5:
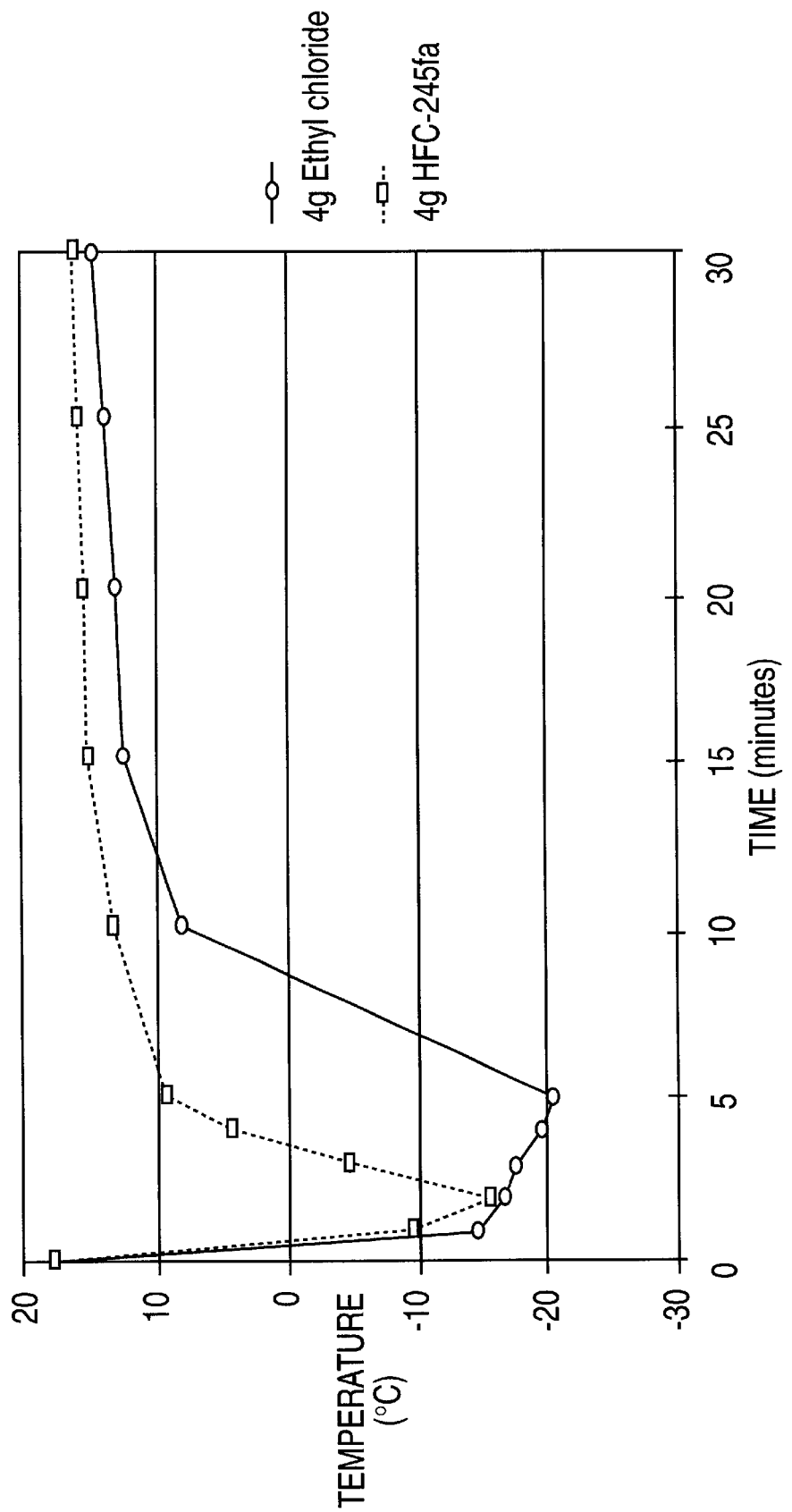
FIG. 5 is a graph comparing the cooling effects of ethyl chloride and 1,1,1,3,3-pentafluoropropane at four grams loading.

From the results depicted in FIGS. 4 and 5, it can be seen that the temperature of the surface recovers to 0° C faster with HFC-245fa than with ethyl chloride. The cooling curves for HFC-245fa are nearly the same at 2 g and 4 g loadings. However, for the cooling curves for ethyl chloride at the two different loadings are quite different. At a 4 g loading, the ethyl chloride surface temperature had fallen below -20° C. The sustained low temperature at the higher 4 g loading of ethyl chloride could result in localized skin freezing. On the other hand, the HFC-245fa recovers to above 0° C. at either the 2 g or 4 g loading well within 5 minutes of spraying.

EXAMPLE 4

A test was conducted to compare the feel of 1,1,1,3,3-pentafluoropropane to ethyl chloride when used as a coolant spray. Samples of each material were sprayed on the skin of a subject and evaluated for cooling effect. The two sprays both provided immediate skin cooling and were found to be indistinguishable from each other.

Having thus described a few particular embodiments of the invention, various alterations, modifications, and improvements will readily occur to those skilled in the art. Such alterations, modifications and improvements as are made obvious by this disclosure are intended to be part of this description though not expressly stated herein, and are intended to be within the spirit and scope of the invention. The foregoing description is by way of example only, and not limiting. The invention is limited only as defined in the following claims and equivalents thereto.

I claim:

1. A method of cooling skin comprising spraying a liquid evaporative coolant containing at least one hydrofluorocarbon or hydrochlorofluorocarbon on the skin, wherein said coolant has a boiling point in the range of about −10° C. to about 25° C. and wherein the at least one hydrofluorocarbon is selected from the group consisting of 1,1,1,3,3-pentafluoropropane, 1,1,2,3,3,3-hexafluoropropane and 1,1,2,2,3,3-hexafluoropropane.

2. The method of claim 1 wherein said coolant consists essentially of one hydrofluorocarbon selected from the group consisting of 1,1,1,3,3-pentafluoropropane, 1,1,2,3,3,3-hexafluoropropane, and 1,1,2,2,3,3-hexafluoropropane.

3. The method of claim 2 wherein said coolant consists essentially of 1,1,1,3,3-pentafluoropropane.

4. The method of claim 1 wherein said coolant contains 1,1,1,3,3-pentafluoropropane and at least one other hydrofluorocarbon or hydrochlorofluorocarbon.

5. The method of claim 4 wherein said coolant contains at least 50 weight percent 1,1,1,3,3-pentafluoropropane and at least one other hydrofluorocarbon or hydrochlorofluorocarbon selected from the group consisting of HFC-134a, HFC-134, HFC-227ea, HFC-227ca, HCFC-124, HCFC-142b, HFC-236fa, HFC-254cb, HFC-236cb, HFC-236ea, and HFC-236ca.

6. The method of claim 5 wherein said coolant is substantially free of hydrochlorofluorocarbons.

* * * * *